United States Patent
Jones et al.

(10) Patent No.: US 9,250,220 B2
(45) Date of Patent: Feb. 2, 2016

(54) SYSTEM FOR PREVENTING UNDUE BENDING OF CABLES

(71) Applicant: International Business Machines Corporation, Armonk, NY (US)

(72) Inventors: Christopher P. Jones, Las Vegas, NV (US); Jonathan Lenchner, North Salem, NY (US); Nathan E. Masters, Henderson, NV (US); James A. Oravec, Las Vegas, NV (US); Rodrigo A. Rey, Las Vegas, NV (US)

(73) Assignee: International Business Machines Corporation, Armonk, NY (US)

( * ) Notice: Subject to any disclaimer, the term of this patent is extended or adjusted under 35 U.S.C. 154(b) by 470 days.

(21) Appl. No.: 13/739,034

(22) Filed: Jan. 11, 2013

(65) Prior Publication Data

US 2014/0150709 A1    Jun. 5, 2014

Related U.S. Application Data

(63) Continuation of application No. 13/692,061, filed on Dec. 3, 2012.

(51) Int. Cl.
  *G01N 31/22* (2006.01)
  *H01B 7/32* (2006.01)
  *H01B 7/36* (2006.01)

(52) U.S. Cl.
  CPC *G01N 31/22* (2013.01); *H01B 7/32* (2013.01); *H01B 7/36* (2013.01)

(58) Field of Classification Search
  CPC ........ G01N 31/22; G02B 6/44; G02B 6/4429; G02B 6/443; H01B 7/32; H01B 7/326; H01B 7/328; H01B 7/36

USPC ........... 116/200, 201, 206; 174/112, 110 R, 174/68.1; 324/537; 356/73.1

See application file for complete search history.

(56) References Cited

U.S. PATENT DOCUMENTS 4,623,218 A * 11/1986 Laurette et al. ............... 385/101
4,883,054 A    11/1989 Fuller et al.
(Continued)

FOREIGN PATENT DOCUMENTS

| CN | 101881677 A | 11/2010 | |
| EP | 2669901 A1 * | 12/2013 | H01B 7/32 |

(Continued)

OTHER PUBLICATIONS

English abstract of JP2009052714 (A).
(Continued)

*Primary Examiner* — R. A. Smith
(74) *Attorney, Agent, or Firm* — Cahn & Samuels, LLP

(57) ABSTRACT

A cable system is disclosed including a central cable; an inner membrane having a higher minimum bend radius than the central cable and surrounding the cable, thereby forming an inner chamber around the central cable, the inner chamber containing a gas or at least one chemical; and an outer membrane surrounding the inner membrane and forming an outer chamber around the inner chamber, the outer chamber comprising a gas or at least one chemical. When the minimum bend radius of the inner membrane is exceeded, the inner membrane fractures or breaks, and the gas or at least one chemical from the inner chamber enters the outer chamber to create a chemiluminescence reaction, color, or smell.

23 Claims, 6 Drawing Sheets

(56) References Cited

U.S. PATENT DOCUMENTS

| | | | |
|---|---|---|---|
| 5,922,996 A * | 7/1999 | Ryeczek | 174/112 |
| 5,982,967 A * | 11/1999 | Mathis et al. | 385/102 |
| 6,108,475 A | 8/2000 | Chapin et al. | |
| 6,207,902 B1 * | 3/2001 | Balaguer | 174/112 |
| 6,559,437 B1 | 5/2003 | Pope, Jr. et al. | |
| 6,596,943 B1 * | 7/2003 | Ward | 174/112 |
| 6,771,359 B2 * | 8/2004 | Beller | 356/73.1 |
| 6,798,956 B2 * | 9/2004 | Morrison | 385/100 |
| 7,027,706 B2 | 4/2006 | Diaz et al. | |
| 7,356,228 B1 | 4/2008 | Berens et al. | |
| 7,473,906 B2 * | 1/2009 | Egalon | 250/458.1 |
| 7,512,299 B2 * | 3/2009 | Berens et al. | 385/100 |
| 7,631,666 B1 * | 12/2009 | Ng et al. | 138/104 |
| 7,826,043 B1 * | 11/2010 | Urban et al. | 356/73.1 |
| 7,954,530 B1 * | 6/2011 | Bennett et al. | 156/358 |
| 2001/0055438 A1 | 12/2001 | Tweedy et al. | |
| 2002/0081082 A1 | 6/2002 | Rossi et al. | |
| 2010/0202726 A1 * | 8/2010 | Egalon | 385/12 |
| 2011/0102766 A1 | 5/2011 | Kunigami et al. | |

FOREIGN PATENT DOCUMENTS

| | | | |
|---|---|---|---|
| JP | 03021853 | 1/1991 | |
| JP | 03077026 A * | 4/1991 | G01J 1/02 |
| JP | 07282644 A * | 10/1995 | H01B 7/32 |
| JP | 2009052714 A | 3/2009 | |

OTHER PUBLICATIONS

English abstract of CN101881677 (A).
English abstract of JP03-21853.
Glow Stick, Wikipedia, http://en.wikipedia.org/w/index.php?title=Glow_stick&printable=yes, printed on Sep. 27, 2012.
Fluorophore, Wikipedia, http://en.wikipedia.org/w/index.php?title=Fluorophore&printable=yes, printed on Sep. 27, 2012.
How Did Mr. Wizard Do an Experiment Where Two Clear Liquids, When Mixed, Suddenly Turned Black?, Yahoo, http://answers.yahoo.com/question/index?qid=20081127223057AAV5oWQ, printed Sep. 27, 2012.
Kuang, Jao-Hwa, et al., "Plastic Optical Fiber Displacement Sensor Based on Dual Cycling Bending," Sensors, 2010, p. 101-98-10210, vol. 10.

* cited by examiner

SYSTEM FOR PREVENTING UNDUE BENDING OF CABLES

This application is a Continuation Application of U.S. Ser. No. 13/692,061, filed on Dec. 3, 2012, in the U.S. Patent and Trademark Office, the entirety of which is incorporated herein by reference.

BACKGROUND

The present invention relates to a cable system and to methods for preventing undue or unwanted bending of a cable.

Modern high bandwidth networking cables, for example fiber-optic cables, have strict limitations on their so-called bend radius. For example, with reference to FIG. 1, a minimum bend radius 100 for an unshielded cable may be about 8 times the cable diameter and a minimum bend radius of a shielded cable may be about 12 times the cable diameter. The minimum bend radius is the radius beyond which a cable should not be bent without risking damage to the integrity of the cable. The minimum bend radius sometimes appears in fine print on the outside of a cable. However, these cables are thicker than ever, and more and more cables are being stuffed into a fixed amount of space around data center racks, in the plenum, or on raised cable guides. Thus, it is inevitable that installers will sometimes try to over-bend the cables and, in the process, compromise the quality or even destroy the cables.

There is therefore a need for cables with strict bend width limitations and methods whereby installers are clearly notified as soon as they attempt to over-bend cables.

BRIEF SUMMARY

According to an embodiment of the present invention, a cable system comprises (1) a central cable; (2) an inner membrane having a higher minimum bend radius than the central cable and surrounding the central cable, thereby creating an inner chamber, the inner chamber containing a gas or at least one chemical; and (3) an outer membrane surrounding the inner membrane and creating an outer chamber, the outer chamber containing a gas or at least one chemical. When the minimum bend radius of the inner membrane is exceeded, the inner membrane fractures or breaks, and the gas or at least one chemical in the inner chamber enters the outer chamber to create a chemiluminescence reaction, a color, or a smell.

According to another embodiment of the present invention, a cable system comprises (1) a central cable; (2) an inner membrane having a higher minimum bend radius than the central cable and surrounding the central cable, thereby creating an inner chamber, the inner chamber containing a gas or at least one chemical; and (3) a clear, transparent, or translucent outer membrane surrounding the inner membrane, thereby creating an outer chamber, the outer chamber containing at least one chemical and a non-excited fluorescent dye. When the inner membrane fractures or breaks, the at least one chemical in the inner chamber is mixed with the at least one chemical and the non-excited fluorescent dye in the outer chamber to create a chemiluminescence reaction.

According to yet another embodiment of the present invention, a cable system comprises (1) a central cable; (2) an inner membrane having a higher minimum bend radius than the central cable and surrounding the central cable, thereby creating an inner chamber, the inner chamber containing a harmless, odiferous gas; and (3) a perforated outer membrane. When the inner membrane fractures or breaks, the gas exits the inner chamber and seeps out through the perforated outer membrane into the atmosphere, thereby creating an observable smell.

According to yet another embodiment of the present invention, a cable system comprises (1) a central cable and (2) a membrane having a higher minimum bend radius than the central cable and surrounding the central cable, thereby creating a chamber, the chamber containing a harmless, odiferous gas. When the membrane fractures or breaks, the odiferous gas exits the chamber and seeps into the atmosphere, thereby creating an observable smell.

According to another embodiment of the present invention, a method for providing a warning when a minimum bend radius of a cable is being approached comprises bending a cable system comprising (1) a central cable; (2) an inner membrane having a higher minimum bend radius than the central cable and surrounding the central cable, thereby creating an inner chamber, the inner chamber comprising a gas or at least one chemical; and (3) an outer membrane surrounding the inner membrane and creating an outer chamber, the outer chamber comprising a gas or at least one chemical; breaking or fracturing the inner membrane; and the gas or at least one chemical in the inner chamber entering the outer chamber, thereby creating a chemiluminescene reaction, a color, or a smell.

According to a further embodiment of the present invention, a method for providing a warning when a minimum bend radius of a cable is being approached comprises bending a cable system comprising (1) a central cable; (2) an inner membrane having a higher minimum bend radius than the central cable and surrounding the central cable, thereby creating an inner chamber, the inner chamber comprising at least one chemical; and (3) a clear, transparent, or translucent outer membrane surrounding the inner membrane and creating an outer chamber, the outer chamber comprising at least one chemical and a non-excited fluorescent dye; breaking or fracturing the inner membrane; and mixing the at least one chemical in the inner chamber with the at least one chemical and the non-excited fluorescent dye in the outer chamber to create a chemiluminescence reaction.

According to yet another embodiment of the present invention, a method for providing a warning when a bend radius of a cable is being approached comprises bending a cable system comprising (1) a central cable; (2) an inner membrane having a higher minimum bend radius than the central cable and surrounding the central cable, thereby creating an inner chamber, the inner chamber comprising a harmless, odiferous gas; and (3) a perforated outer membrane surrounding the inner membrane; breaking or fracturing the inner membrane; and the odiferous gas exiting the perforated outer membrane, thereby creating an observable smell.

According to another embodiment of the present invention, a method for providing a warning when a bend radius of a cable is being approached comprises bending a cable system comprising (1) a central cable; and (2) a membrane having a higher minimum bend radius than the central cable and surrounding the central cable, thereby creating a chamber, the chamber comprising a harmless, odiferous gas; breaking or fracturing the membrane; and the odiferous gas exiting the membrane, thereby creating an observable smell.

DETAILED DESCRIPTION

According to the present invention, a central cable is encased with, or surrounded by, two membranes or sheaths. A first, inner membrane surrounds the central cable and creates an inner chamber. The inner membrane may be made of a fractureable material, including but not limited to, glass, glass fibers, plastic, or ceramic. The inner membrane has a higher minimum bend radius than that of the central cable itself. A second, outer membrane surrounds the inner membrane and creates an outer chamber. The outer membrane may be made of a clear, transparent, or translucent material, including but not limited to, a plastic, glass, or polymer material. In specific embodiments, the outer membrane may be substantially non-fractureable.

According to the present invention, in specific embodiments, the inner chamber and outer chamber may each contain a gas or at least one chemical compound or substance. When the minimum bend radius of the inner membrane is exceeded, the inner membrane breaks or fractures. Upon fracture of the inner membrane, the gas or at least one chemical of the inner chamber enters the outer chamber and/or vice versa to create a chemilumiescence reaction, a color, or a smell. In specific embodiments, the chemicals of the inner chamber and the outer chamber are chosen so that, when mixed, they produce a chemiluminescence reaction, or a chemically-induced light emission, thereby signaling that the cable system (e.g., central cable and inner and outer membranes) cannot, or should not, be further bent because the minimum bend radius of the central cable is being approached.

Figure 1:
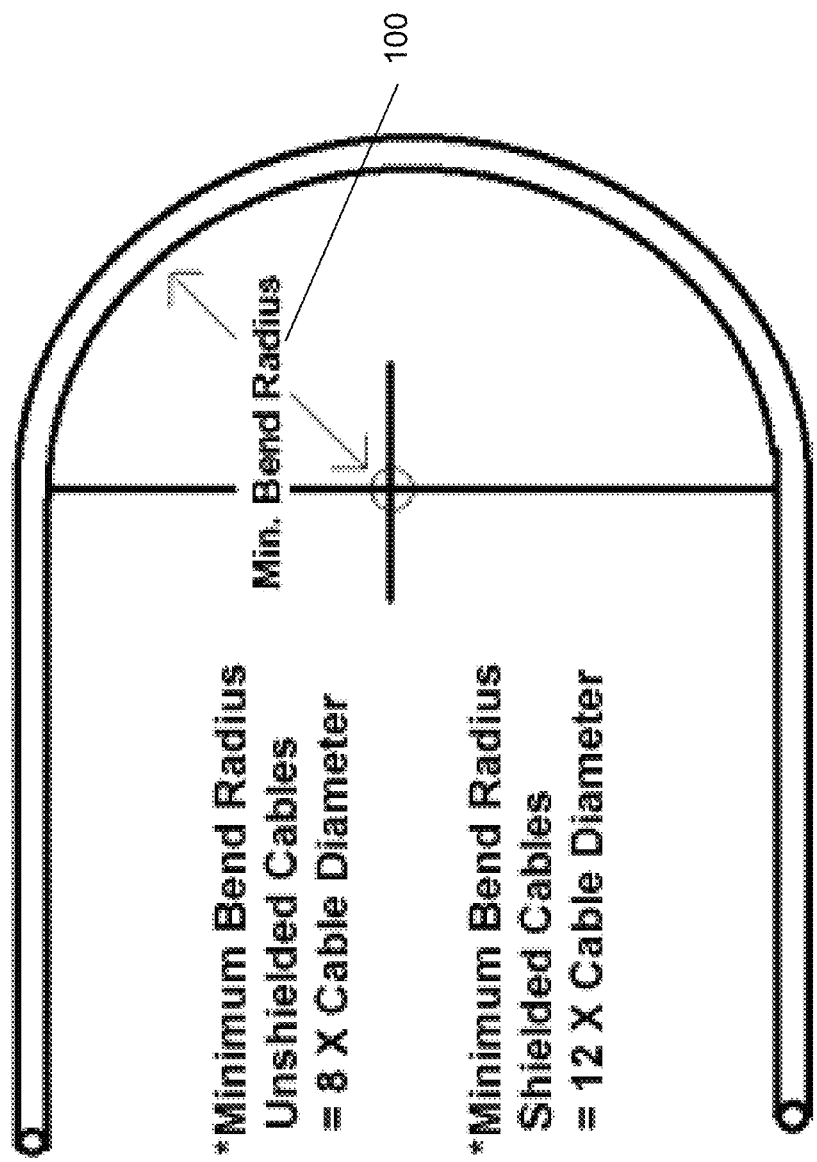
FIG. 1 is a schematic diagram showing a minimum bend radius of a cable.
Figure 2:
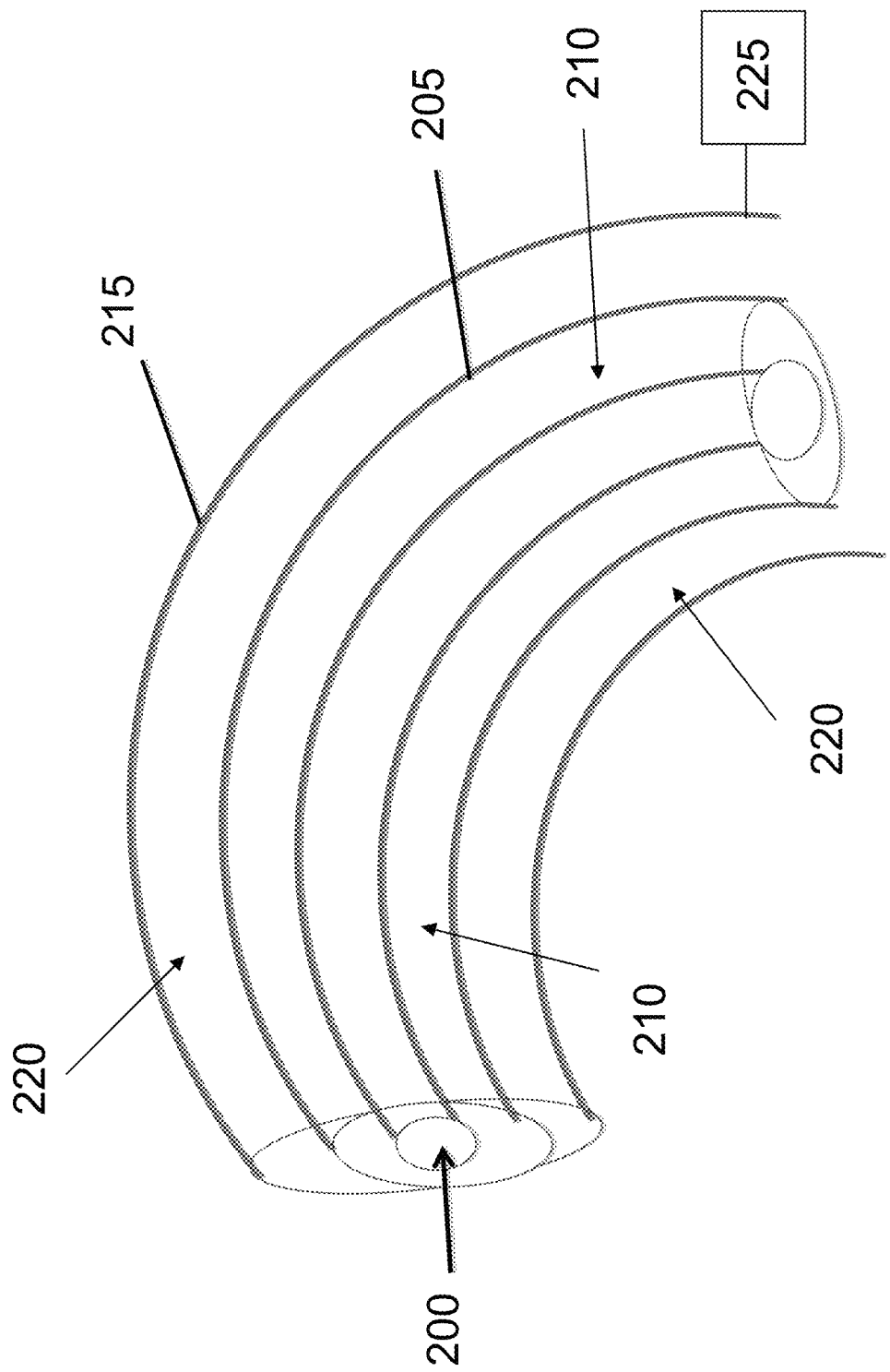
FIG. 2 is a schematic diagram of a cable system having an inner membrane creating an inner chamber and an outer membrane creating an outer chamber according to an embodiment of the present invention.

With reference now to FIG. 2, a central cable 200 has a minimum bend radius, for example, $\lambda$. An inner membrane 205 surrounds the cable 200 and creates an inner chamber 210. The inner membrane 205 has a minimum bend radius, for example, $\lambda+\epsilon$, where, in a specific embodiment, $\epsilon$ may be about $0.1\lambda$.

In a specific embodiment of the present invention, an inner chamber 210 created by the inner membrane 205 may contain at least one chemical, for example, hydrogen peroxide. An outer membrane 215 surrounds the inner membrane 205 and creates an outer chamber 220. The outer chamber 220 may comprise at least one chemical, such as a diphenyl oxalate, and a (non-excited) fluorescent dye. When the inner membrane 205 begins to fracture, the diphenyl oxalate and fluorescent dye from the outer chamber 220 mixes with the hydrogen peroxide from the inner chamber 210, thereby causing a chemiluminescence reaction. For example, the chemical reaction may yield two molecules of phenol and one molecule of peroxyacid ester (1,2-dioxetanedione). The peroxyacid ester decomposes spontaneously to carbon dioxide, releasing energy that excites the fluorescent dye, which then releases a photon. The wavelength of the photon (i.e., the color of the emitted light) depends on the particular dye used. Such fluorescent dyes, known as fluorophores, each may have a different characteristic wavelength (e.g., emitting light in the visible, infrared, or ultraviolet spectrum).

In a specific embodiment of the present invention, in order that the fluorescent dye not be quickly dissipated, the cable system may be divided into a plurality of distinct sections, for example in the range of about 1 to about 2 feet per section, with separating walls to prevent the fluorescence from dissipating throughout the length of the cable system. This structure may be useful in cases where excessive bending of the cable system is confined to a small section and/or to make sure that excessive bending is recognized even if not caught immediately, by virtue of the fact that the fluorescence is contained and not dissipated.

Figure 3:
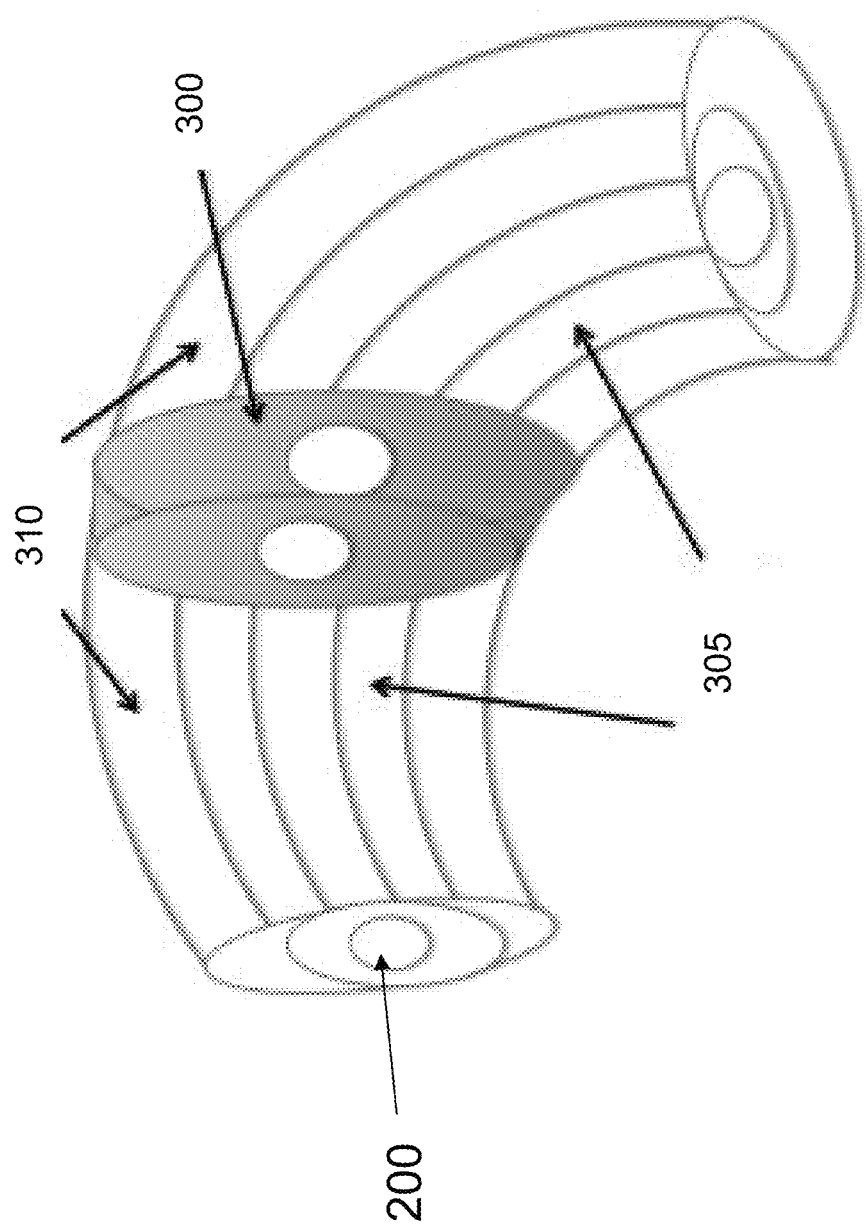
FIG. 3 is a schematic diagram of a cable system having separating walls according to an embodiment of the present invention.
Figure 4:
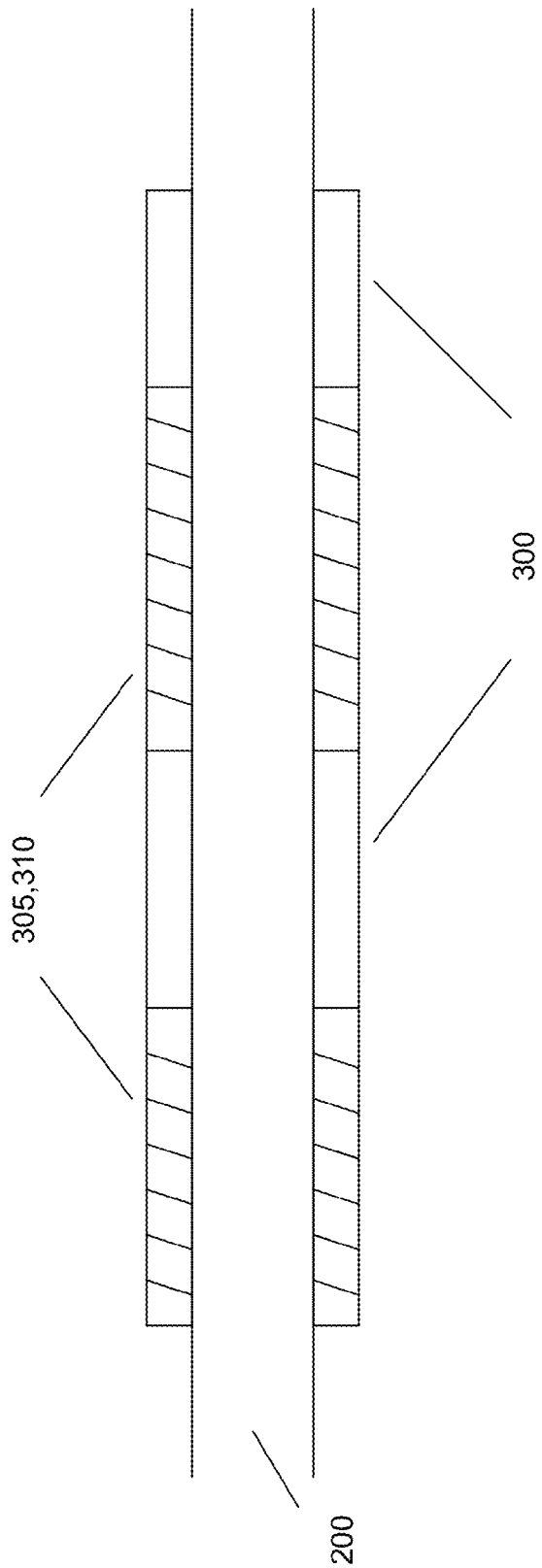
FIG. 4 is a schematic top view of a cable system of FIG. 3.

With reference now to FIGS. 3-4, at least one pair of separating walls 300 may be added to the cable system to isolate at least one section 305 of the inner chamber 210 surrounding central cable 200 and at least one section 310 of the outer chamber 220. When the minimum bend radius of the at least one section of the inner membrane is exceeded and the inner membrane fractures or breaks, the resulting chemiluminescence reaction is confined to sections 305, 310. Thus, the resulting fluorescent light does not dissipate quickly. In specific embodiments, the separating walls 300 may comprise double-walled sections between which the inner and outer chambers are free of chemicals.

In specific embodiments, the separating walls 300 may be made of any material that will not be compromised by bending or flattening, but can easily be cut through, for example, a plastic or polymer material. In the event that the central cable 200 needs to be cut (e.g., to get rid of a compromised section which has already undergone chemiluminescence, sections 305, 310), a cut may be made within or between a pair of separating walls 300. According to an embodiment of the present invention, the location of separating walls 300 may be appropriately indicated, for example, by externally printed, raised, or embossed markings which contrast with a clear, transparent, or translucent outer membrane found elsewhere along a length of the cable system.

In another embodiment of the present invention, the at least one chemical of the inner chamber and the at least one chemical of the outer chamber mix to create a colored reaction or compound, rather than a chemiluminescence reaction.

According to an embodiment of the present invention, the cable system may comprise a sensor (225 in FIG. 2). The sensor 225 may be at least one of an optical or spectrophotometric sensor. The sensor 225 may have the ability to detect a change in color and/or light caused by the fracture or rupture of the inner membrane and provide a visual and/or audible warning, for example, to an installer.

In yet another embodiment of the present invention, an outer membrane may comprise a perforated material, and an inner chamber may contain a harmless, odiferous gas observable via a human olfactory sense. The gas may include, but is not limited to, methyl mercaptan and/or ethyl mercaptan. Such gases are often added to natural gas to give it an especially noticeable smell in the event of a leak. In a specific embodiment, the odiferous gas may comprise ammonium sulfide, which provides a recognizable rotten-eggs smell. This embodiment may be advantageous in cases where potentially excessive cable bending takes place out of sight of an installer and a chemiluminescence reaction would be unobserved (e.g., when one or more cables are jammed into a sub-floor). In this embodiment, it is not necessary for the perforated outer membrane to be made of a clear, transparent, or translucent material.

In another embodiment of the present invention, the cable system may comprise a single membrane surrounding the central cable thereby creating a chamber, the chamber containing a harmless, odiferous gas observable via a human olfactory sense. The gas may include but is not limited to, methyl mercaptan, ethyl mercaptan, or ammonium sulfide. When the membrane fracture or breaks, the odiferous gas escapes into the atmosphere or environment where it can be smelled.

Figure 5:
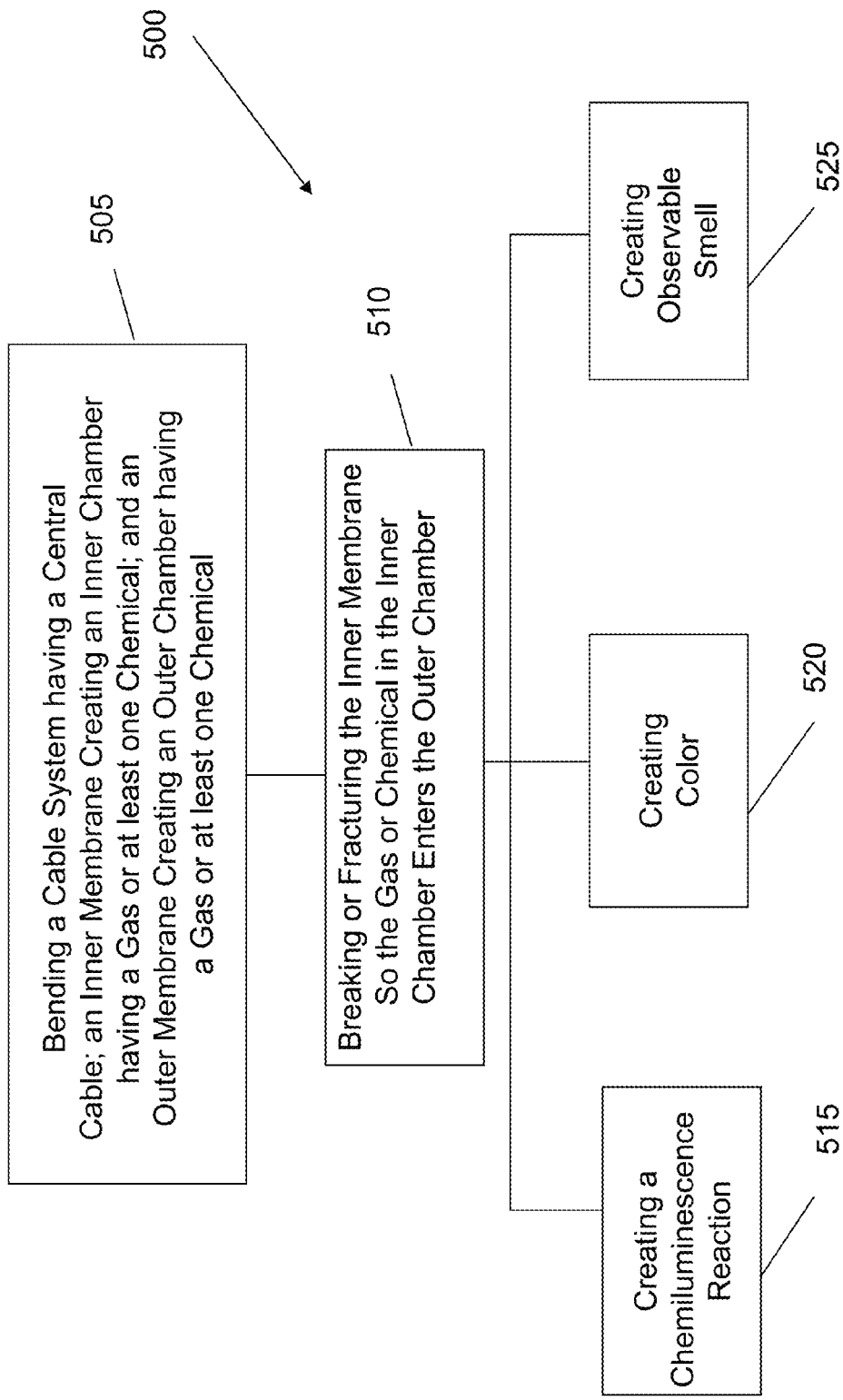
FIG. 5 illustrates a method for providing a warning when a bend radius of a cable is being approached according to at least one embodiment of the present invention.

With reference now to FIG. 5, a method 500 for providing a warning when a minimum bend radius of a cable is being approached, according to the present invention, includes bending a cable system, 505, comprising 1) a central cable; 2) an inner membrane having a higher minimum bend radius than the central cable and surrounding the central cable, thereby creating an inner chamber, the inner chamber comprising a gas or at least one chemical; and 3) an outer membrane surrounding the inner membrane, creating an outer chamber; breaking or fracturing the inner membrane, 510; such that the gas or at least one chemical in the inner chamber enters the outer chamber and/or vice versa, thereby creating a chemiluminescence reaction, 515; color, 520; or observable smell 525.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 6:
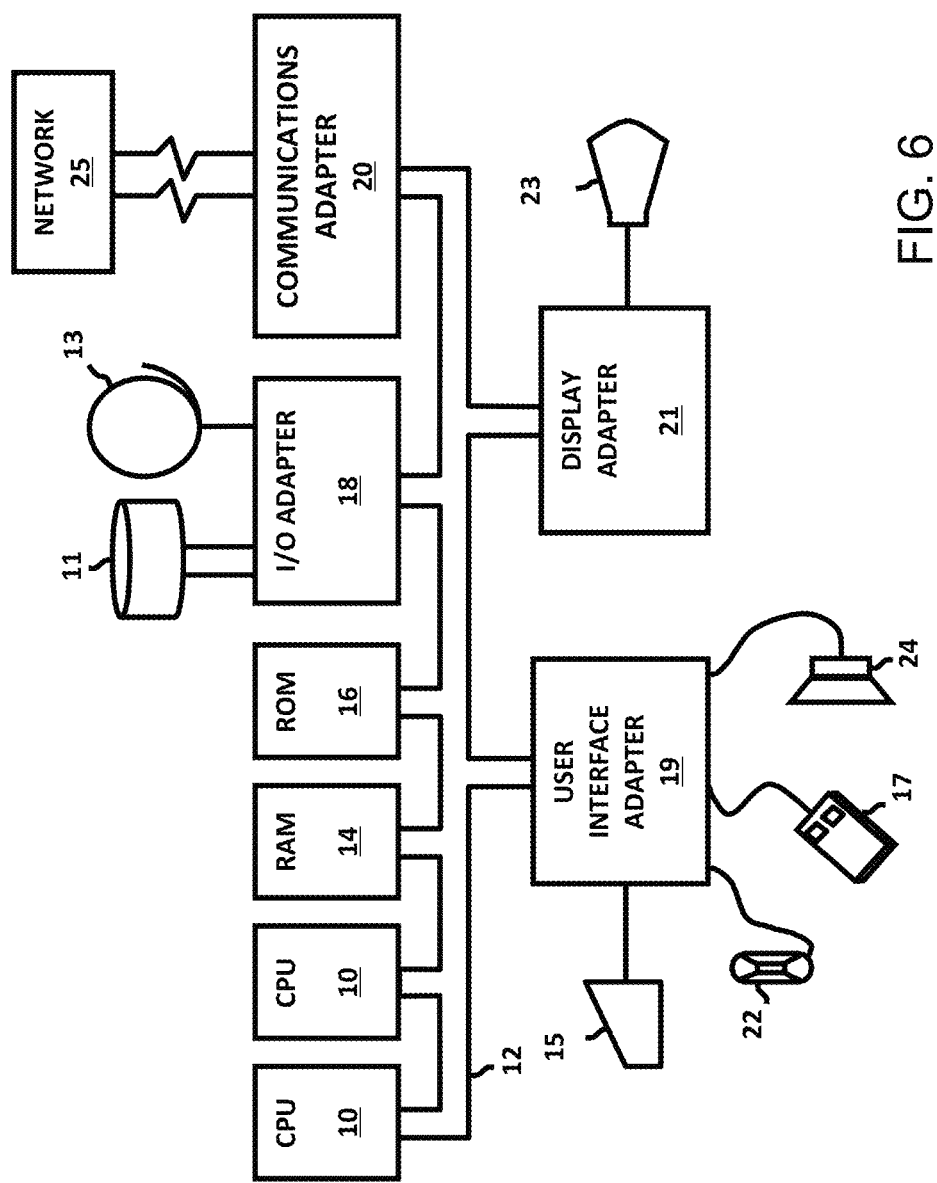
FIG. 6 illustrates a hardware environment for practicing at least one embodiment of the present invention.

Referring now to FIG. 6, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for providing a warning when a minimum bend radius of a cable is being approached, comprising:
   bending a cable system comprising (1) a central cable; (2) an inner membrane having a higher minimum bend radius than the central cable and surrounding the central cable, thereby creating an inner chamber, the inner chamber comprising a gas or at least one chemical; (3) an outer membrane surrounding the inner membrane and creating an outer chamber, the outer chamber comprising a gas or at least one chemical; and (4) at least one pair of separating walls that isolate at least one section of the inner chamber and at least one section of the outer chamber surrounding the central cable, wherein the at least one pair of separating walls comprise a double-walled section between which the inner and outer chambers are free of any reactive gases or chemicals;
   breaking or fracturing the inner membrane; and
   said gas or at least one chemical in the inner chamber entering the outer chamber, thereby creating a chemiluminescene reaction, a color, or a smell.

2. A method according to claim 1, further comprising detecting said chemiluminescene reaction or color with a sensor.

3. A method for providing a warning when a minimum bend radius of a cable is being approached, comprising:
   bending a cable system comprising (1) a central cable; (2) an inner membrane having a higher minimum bend radius than the central cable and surrounding the central cable, thereby creating an inner chamber, the inner chamber comprising at least one chemical; (3) a clear, transparent, or translucent outer membrane surrounding the inner membrane, thereby creating an outer chamber, the outer chamber comprising at least one chemical and a non-excited fluorescent dye; and (4) at least one pair of separating walls that isolate at least one section of the inner chamber and at least one section of the outer chamber surrounding the central cable, wherein the at least one pair of separating walls comprise a double-walled section between which the inner and outer chambers are free of any reactive gases or chemicals;
   breaking or fracturing the inner membrane; and
   mixing the at least one chemical in the inner chamber with the at least one chemical and the non-excited fluorescent dye in the outer chamber to create a chemiluminescence reaction.

4. A method according to claim 3, wherein the inner membrane comprises a fractureable material.

5. A method according to claim 4, wherein the fractureable material comprises glass, plastic, or ceramic.

6. A method according to claim 3, wherein the at least one chemical in the inner chamber comprises hydrogen peroxide.

7. A method according to claim 3, wherein the outer membrane comprises a non-fractureable material.

8. A method according to claim 7, wherein the outer membrane comprises a plastic, glass, or polymer material.

9. A method according to claim 7, wherein the outer membrane comprises glass fiber.

10. A method according to claim 3, wherein the at least one chemical in the outer chamber comprises diphenyl oxideate and a fluorescent dye.

11. A method according to claim 3, wherein the at least one section comprises a plurality of sections.

12. A method according to claim 3, wherein said cable system further comprises at least one marking on an exterior of the outer membrane to indicate a location of the at least one pair of separating walls.

13. A method according to claim 3, further comprising cutting the cable system between said at least one pair of separating walls.

14. A method according to claim 3, further comprising detecting said chemiluminescence reaction with a sensor.

15. A cable system according to claim 3, wherein the central cable is not a fiber optic cable.

16. A method for providing a warning when a bend radius of a cable is being approached, comprising:
    bending a cable system comprising (1) a central cable; (2) an inner membrane having a higher minimum bend radius than the central cable and surrounding the central cable, thereby creating an inner chamber, the inner chamber comprising a harmless, odiferous gas; and (3) a perforated outer membrane surrounding the inner membrane; breaking or fracturing the inner membrane; and (4) at least one pair of separating walls that isolate at least one section of the inner chamber, wherein the at least one pair of separating walls comprise a double-walled section which is free of any reactive gases or chemicals; and
    the odiferous gas exiting the perforated outer membrane, thereby creating an observable smell.

17. A method according to claim 16, wherein said bending and/or breaking occurs out of sight of an installer.

18. A method according to claim 16, wherein the inner membrane comprises a fractureable material.

19. A method according to claim 18, wherein the fractureable material comprises glass, plastic, or ceramic.

20. A method according to claim 16, wherein the odiferous gas comprises methyl mercaptan or ethyl mercaptan.

21. A method according to claim 16, wherein the odiferous gas comprises ammonium sulfide.

22. A method according to claim 16, wherein the central cable is not a fiber optic cable.

23. A method for providing a warning when a bend radius of a cable is being approached, comprising:
- bending a cable system comprising (1) a central cable; (2) a membrane having a higher minimum bend radius than the central cable and surrounding the central cable, thereby creating a chamber, the chamber comprising a harmless, odiferous gas; and (3) at least one pair of separating walls that isolate at least one section of the chamber, wherein the at least one pair of separating walls comprise a double-walled section which is free of any reactive gases or chemicals;
- breaking or fracturing the membrane; and
- the odiferous gas exiting the membrane, thereby creating an observable smell.

* * * * *